US011591343B2

(12) United States Patent
Pouyet et al.

(10) Patent No.: US 11,591,343 B2
(45) Date of Patent: Feb. 28, 2023

(54) THERMOLYSIS-MEDIATED PROCESS FOR MANUFACTURING CHROMENES INTENDED FOR THE PREPARATION OF THERMOSETTING RESINS

(71) Applicants: ARIANEGROUP SAS, Paris (FR); CENTRE NATIONAL DE LA RECHERCHE SCIENTIFIQUE, Paris (FR); UNIVERSITE DE REIMS CHAMPAGNE-ARDENNE, Reims (FR)

(72) Inventors: Robin Pouyet, Le Haillan (FR); Xavier Coqueret, Reims (FR); Brigitte Defoort, Le Haillan (FR); Bastien Rivieres, Le Segur (FR)

(73) Assignees: ARIANEGROUP SAS, Paris (FR); CENTRE NATIONAL DE LA RECHERCHE SCIENTIFIQUE, Paris (FR); UNIVERSITE DE REIMS CHAMPAGNE-ARDENNE, Reims (FR)

( * ) Notice: Subject to any disclaimer, the term of this patent is extended or adjusted under 35 U.S.C. 154(b) by 0 days.

(21) Appl. No.: 16/936,915

(22) Filed: Jul. 23, 2020

(65) Prior Publication Data
US 2021/0024533 A1 Jan. 28, 2021

(30) Foreign Application Priority Data
Jul. 23, 2019 (FR) ...................................... 1908324

(51) Int. Cl.
*C07D 493/02* (2006.01)
*C07D 493/04* (2006.01)

(52) U.S. Cl.
CPC ................... *C07D 493/04* (2013.01)

(58) Field of Classification Search
CPC .................................................. C07D 493/02
See application file for complete search history.

(56) References Cited

U.S. PATENT DOCUMENTS

| 5,155,196 | A | 10/1992 | Kolb et al. | |
|---|---|---|---|---|
| 2021/0024534 | A1* | 1/2021 | Pouyet | C08G 61/122 |
| 2021/0024535 | A1* | 1/2021 | Pouyet | C08G 61/122 |

FOREIGN PATENT DOCUMENTS

| EP | 0 350 747 A2 | 1/1990 | |
|---|---|---|---|
| WO | WO 01/10861 A2 | 2/2001 | |
| WO | WO 2017/129661 A1 | 8/2017 | |
| WO | WO-2017129661 A1 * | 8/2017 | ............... B64G 1/58 |

OTHER PUBLICATIONS

Menon, Rajeev S., et al. "The Au(I)-Catalyzed Intramolecular Hydroarylation of Terminal Alkynes Under Mild Conditions: Application to the Synthesis of 2H-Chromenes, Coumarins, Benzofurans, and Dihydroquinolines." J. Org. Chem. (2009), vol. 74, pp. 8901-8903 . (Year: 2009).*
Search Report as issued in French Patent Application No. 1908324, dated Jul. 7, 2020.
Al-Sader et al., "On the Mechanism of Flash Vacuum Pyrolysis of Phenyl Propargyl Ether. Intramolecular Deuterium Kinetic Isotope Effect on Claisen Rearrangement," J. Org. Chem., vol. 43, No. 18, (1978), XP55701628, pp. 3626-3627.
Parker, K. A., et al., "Electrocyclic Ring Closure of the Enols of Vinyl Quinones. A 2H-Chromene Synthesis," Organic Letters, vol. 3, No. 24, (2001), XP55701593, pp. 3875-3878.
Christoudoulou, M. S., et al., "Divergent Palladium- and Platinum-Catalyzed Intramolecular Hydroamination/Hydroarylation of O-Propargyl-2-aminophenols," European Journal of Organic Chemistry, vol. 44, Jul. 2018, XP055693802, pp. 6176-6184, Retrieved from the Internet: URL:https://chemistry-europe.onlinelibrary.wiley.com/doi/full/10.1002/ejoc.201801103 [Retrieved on May 11, 2020].
Menon, R. S., et al., "The AU(I)-catalyzed Intramoleoular hydroarylation of Terminal Alkynes Under Mild Conditions: Application to the Synthesis of 2H-Chromenes, Coumarins, Benzofurans, and Dihydroquinolines," J. Org. Chem., vol. 74, (2009), XP55082760, pp. 8901-8903.
Arcadi, A., et al. "Gold versus silver 1-7 catalyzed intramolecular hydroarylation reactions of [(3-arylprop-2-ynyl)oxy]benzene derivatives," Organic & Biomolecular Chemistry, vol. 10, No. 48, Jan. 2012, XP55700971, pp. 9700-9708.
Fang, W., et al., "Gold(I) catalyzed intramolecular hydroarylation and the subsequent ring enlargement of methylenecyclopropanes to cyclobutenes," RSC Advances, vol. 6, No. 46, Jan. 2016, XP55701069, pp. 40474-40479.
Liu, F., et al., "Blended Resins Based on a New Propargyl-Functional Resin: Synthesis, Cure, and Thermal Properties," Journal of Applied Polymer Science, vol. 102, pp. 4207-4212, (2006).
Hashmi, et al., "Modern Gold Catalyzed Synthesis," Wiley-VCH Verlag & Co. KGaA, (2012), 408 pages.
Godschaix, J. P., et al., "Acetylene-Chromene Terminated Resins as High Temperature Thermosets," 22$^{nd}$ International SAMPE Technical Conference, Nov. 1990, pp. 163-174.
Reghunadhan, C. P., et al., "Bis propargyl ether resins: synthesis and structure-thermal property correlations," European Polymer Journal 35 (1999) 235-246.
Dirlikov, S. K., et al., "Propargyl-terminated Resins—A Hydrophobic Substitute for Epoxy Resins," High Performance Polymers, vol. 2, No. 1, (1990), pp. 67-77.

(Continued)

*Primary Examiner* — John S Kenyon
(74) *Attorney, Agent, or Firm* — Pillsbury Winthrop Shaw Pittman LLP

(57) ABSTRACT

A process for manufacturing chromenes which are intended for the preparation of thermosetting resins, includes transforming an aromatic propargyl ether of general formula (I) into a chromene by flash vacuum thermolysis, at a temperature of between 300 and 600° C., at a pressure of between 4 and 10,000 Pa. It also concerns a process for preparing a material made of thermoset resin, including successively: a) implementation of the above process; b) polymerization of the reaction product obtained in a) so as to obtain the material made of thermoset resin; c) recovery of the material made of thermoset resin obtained in b).

14 Claims, No Drawings

(56) References Cited

OTHER PUBLICATIONS

Prat, D., et al., "CHEM21 selection guide of classical- and less classical-solvents," Green Chem., (2016), 18, pp. 288-296.

Dirlikov, S. K., et al., "Propargyl Terminated Resins (PTR): Preparation and Thermostability," Polym. Mater., vol. 59, (1988), pp. 990-993.

Efe, C., e al., "Gold nanopanicles supported on TiO2 catalyse the cycloisomerisation/oxidative dimerisation of aryl propargyl ethers," Chem. Commun., (2011), vol. 47, pp. 803-805.

Echavarren, A. M., et al., "Chapter 1: Gold-Catalyzed Cyclizations of Alkynes With Alkenes and Arenes," Organic Reactions, vol. 92, (2017), 288 pages.

Dorel, R., et al., "Gold(I)-Catalyzed Activation of Alkynes for the Construction of Molecular Complexity," Chemical Reviews, (2015), vol. 115, pp. 9028-9072.

Rehman, H., et al., "Tandem Intramolecular Wittig and Claisen Rearrangement Reactions in the Thermolysis of 2-Methyl-2-Phenoxy-Propionyl-Cyanomethylenetriphenylphosphoranes: Synthesis of Substituted 2H-I-Benzopyrans and Benzofurans," Tetrahedron, vol. 43, No. 22, pp. 5335-5340, (1987).

Rehman, H., et al., "Synthesis of Benzofurans Via Tandem Intramolecular Wittig and 3,3-Sigmatropic Reaction of Phenoxyacetyl-Cyanomethylenetriphenylphosphoranes," Synthetic Communications: An International Journal for Rapid Communication of Synthetic Organic Chemistry, (2006), 12 pages.

Ullenius, C., et al., "Formation of 2-Indanone and Benzocyclobutene from the Pyrolysis of Phenyl Ether," Department of Chemistry, University of Oregon, (1972), pp. 5911-5913.

Lazar, K. L., et al., "Optically detected magnetic resonance of α-deuterated 2-indanone," Journal of Luminescence, vol. 118, (2006), pp. 21-32.

Trahanovsky, W. S., et al., "Organic Oxalates. II. Formation of Bibenzyls by Pyrolysis of Benzyl Oxalates," Journal of the American Chemical Society, 90(11), (1968), pp. 2839-2842.

Sanglar, C., "Prepolymers a Terminaisons Propargylique et Chromene. Synthese, Etudes Physicochimiques, Mecanismes et Cinetique D_E polymerisation a L'Etat Fondu." Doctoral Thesis from L'Universite de Pau et des Pays de L'Adour, Centre Universitaire de Recherche Scientifique, Mention: Physicochimie des Polymers, Nov. 13, 1995, 132 pages, (with translation of relevant portions).

\* cited by examiner

THERMOLYSIS-MEDIATED PROCESS FOR MANUFACTURING CHROMENES INTENDED FOR THE PREPARATION OF THERMOSETTING RESINS

CROSS REFERENCES TO RELATED APPLICATIONS

This application claims priority to French Patent Application No. 1908324, filed Jul. 23, 2019, the entire content of which is incorporated herein by reference in its entirety.

The present invention relates to the field of thermosetting resins and to materials obtained from these resins. These resins are directed towards replacing phenolic resins in all the applications in which they are normally used, and notably "ablative" materials.

An ablative material is defined as being a material that can undergo ablation, i.e. a loss of substance by chemical decomposition, change of state or mechanical erosion under the effect of a flow of material or of radiation (Official Journal of the French Republic of 22 Sep. 2000). This is in particular the case for materials included in the construction of heat shields intended for the aerospace industry and the walls of propulsion engine exhaust nozzles. Typically, in this case, the outer layer of the ablative material which is in direct contact with the environment undergoes a chemical transformation under the effect of heat, and also a recession associated with this transformation. This outer layer thus radiates outwards and its chemical transformation consumes energy. These two effects contribute towards reduced heat transmission towards the inner layers of the material and thus to thermal insulation of the underlying structure. A good ablative material must be such that its chemical transformation under the effect of heat is endothermic, its thermal conductivity is low in a stationary and/or transitional regime and its chemical transformation is not accompanied by excessively rapid recession. In particular, to fulfil this last point, it is necessary for the chemical transformation of the ablative material to be accompanied by the formation of a crust based on carbon or silica originating from the pyrolysis of the resin.

This is in particular obtained for resins with a high coke content. The coke content is defined as the mass of residue that is obtained when a sample of an organic polymer is decomposed by pyrolysis, at a temperature of 900° C. under an inert atmosphere (nitrogen or argon), relative to the initial mass of this sample. The most beneficial resins have a coke content of greater than 50%.

Phenolic resins generally have such a coke content and are obtained by polycondensation of petrochemistry-based monomers: phenol and formaldehyde, which explains why they are also known as phenol-formaldehyde resins or formophenolic resins. The precursors of phenolic resins, phenol and formaldehyde, are, respectively, CMR 2 and 1B. These two compounds are thus monitored under Regulation (EC) No. 1907/2006 of the European Parliament (REACH) which is directed towards better protecting human health and the environment against the risks associated with chemical substances. It furthermore turns out that the polycondensation of phenol and formaldehyde is never complete, which accounts for the presence of volatile compounds and of water molecules that are very difficult to remove if a well-defined thermal cycle is not followed during this polycondensation and which may lead to materials that are porous in their native state and also to degassing events during the lifetime of the materials manufactured from phenolic resins. Now, this degassing events may have very harmful consequences in certain applications, for instance aerospace applications.

Given the current importance of phenolic resins in the plastics industry and the drawbacks thereof, novel thermosetting resins with properties similar to those of phenolic resins were obtained from different precursors. Thus, patent application WO 2017/129 661 describes such resins and processes for manufacturing same. Such resins have a coke content of greater than 50% and may thus be used as ablative materials. The precursors used are in particular aromatic molecules bearing propargyl ether functions. However, the excessive amount of energy released during their polymerization could lead to a thermal runaway during the manufacture of composite materials. Thus, in order to obtain an enthalpy of polymerization of about 800-900 J/g with a loss of mass that is as low as possible during the polymerization, it is necessary in the process described in said application to maintain a lengthy thermal treatment throughout the polymerization in order to prevent any thermal runaway. This solution is thus not optimized with respect to the manufacture of thick parts which may be up to several tens of millimetres thick.

The inventors realised that it was possible to reduce the energy released during the polymerization of resins bearing propargyl ether end groups by a factor of 6 by conversion of the propargyl ether function into a chromene function and thus to lower the enthalpy of polymerization to a value <500 J/g.

The inventors realised, surprisingly, that it is possible to perform such a conversion by means of a novel thermolysis process. The aim of this synthesis route is to dispense with the use of a potentially toxic and expensive catalyst, by intense and brief heating of the propargyl ether functions.

Thermolysis processes have already been described in the prior art, using compounds bearing propargyl ether functions, but without managing to obtain chromenes (Al-Sader et al., J. Org. Chem., 1978, Vol. 43, No. 18, Communications, pages 3626-3627 and Trahanovsky et al., 1968, Journal of the American Chemical Society, 90(11), 2839-2842). The inventors realised that it is possible to obtain chromenes during the use of such a process by using particular starting materials.

The present invention thus relates to a process for manufacturing chromenes which are intended for the preparation of thermosetting resins, comprising the step of transforming an aromatic propargyl ether of general formula (I) below

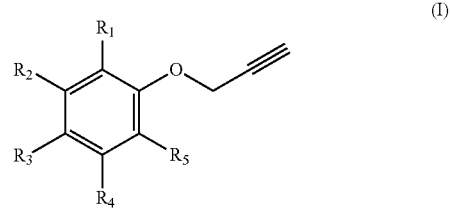

in which:

$R_1$ and $R_5$ represent, independently of each other, a hydrogen atom, a $C_2$-$C_6$ alkene, $C_2$-$C_6$ alkyne, O—($C_1$-$C_6$) alkyl, O—($C_2$-$C_6$)alkene or O—($C_2$-$C_6$)alkyne group group, on condition that at least one from among $R_1$ and $R_5$ represents a hydrogen atom;

$R_2$ and $R_4$ represent, independently of each other, a hydrogen atom, a $C_2$-$C_6$ alkene, $C_2$-$C_6$ alkyne such as propargyl, O—(C$_1$-C$_6$)alkyl, O—(C$_2$-C$_6$)alkene or O—(C$_2$-C$_6$)alkyne such as an O-propargyl;

and R$_3$ represents a hydrogen atom, a O—(C$_1$-C$_6$)alkyl or a C$_2$-C$_6$ alkene group, the alkene group being optionally substituted with a group of general formula (II) below

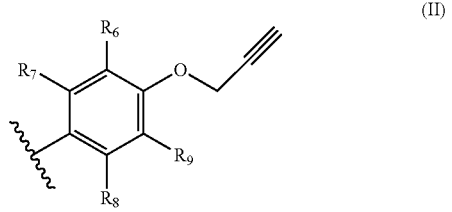

in which:

R$_6$ and R$_9$ represent, independently of each other, a hydrogen atom, a C$_2$-C$_6$ alkene, C$_2$-C$_6$ alkyne, O—(C$_1$-C$_6$) alkyl, O—(C$_2$-C$_6$)alkene or O—(C$_2$-C$_6$)alkyne group, on condition that at least one from among R$_6$ and R$_9$ represents a hydrogen atom;

and R$_7$ and R$_8$ represent, independently of each other, a hydrogen atom, a C$_2$-C$_6$ alkene, C$_2$-C$_6$ alkyne such as propargyl, O—(C$_1$-C$_6$)alkyl, O—(C$_2$-C$_6$)alkene or O—(C$_2$-C$_6$)alkyne such as an O-propargyl;

on condition that at least one from among R$_1$, R$_2$, R$_3$, R$_4$ and R$_5$ does not represent a hydrogen atom or a O—(C$_1$-C$_6$)alkyl group;

and the cis/trans isomers thereof and the optical isomers thereof and the racemic mixtures thereof into a chromene by flash vacuum thermolysis, at a temperature of between 300 and 600° C., beneficially between 400 and 450° C., at a pressure of between 3 and 10,000 Pa, beneficially between 4 and 10000 Pa, more beneficially between 5 and 7000 Pa.

For the purposes of the present invention, the term "C$_2$-C$_6$ alkene group" means any linear or branched alkene group of 2 to 6 carbon atoms, in particular the vinyl group, the allyl group or the 2-butenyl group.

For the purposes of the present invention, the term "C$_2$-C$_6$ alkyne group" means any linear or branched alkyne group of 2 to 6 carbon atoms, in particular the ethynyl group or the propargyl group.

For the purposes of the present invention, the term "O—(C$_1$-C$_6$)alkyl group" means any linear or branched O-alkyl group of 1 to 6 carbon atoms, in particular the methoxy or ethoxy group.

For the purposes of the present invention, the term "O—(C$_2$-C$_6$)alkene group" means any linear or branched 0-alkene group of 2 to 6 carbon atoms.

For the purposes of the present invention, the term "O—(C$_2$-C$_6$)alkyne group" means any linear or branched 0-alkyne group of 2 to 6 carbon atoms, in particular the 0-propargyl group.

Beneficially, the aromatic propargyl ether of general formula (I) is chosen from the group consisting of propargylated resorcinol, propargylated eugenol, propargylated coupled eugenol, propargylated coupled isoeugenol, propargylated isoeugenol and mixtures thereof and the cis/trans isomers thereof and the optical isomers thereof and the racemic mixtures thereof; more beneficially, it is propargylated resorcinol. These products are well known to those skilled in the art and may be prepared via well-known processes, such as those described in patent application WO 2017/129661. They have the benefit of being able to be obtained from compounds that can be biosourced such as resorcinol, eugenol, coupled eugenol, isoeugenol and coupled isoeugenol.

Propargylated resorcinol thus has the following general formula:

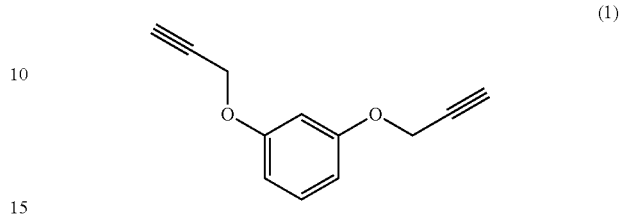

Propargylated eugenol thus has the following general formula:

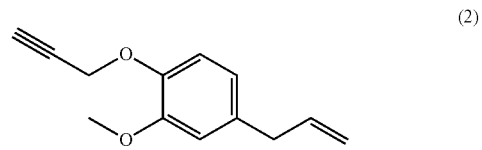

Propargylated coupled eugenol thus has the following general formula:

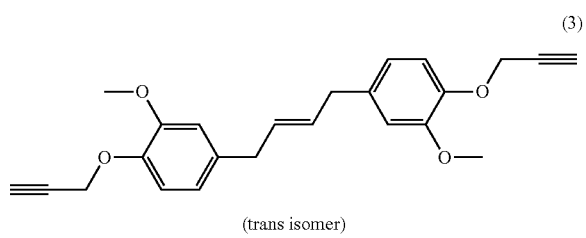

(trans isomer)

or the following general formula

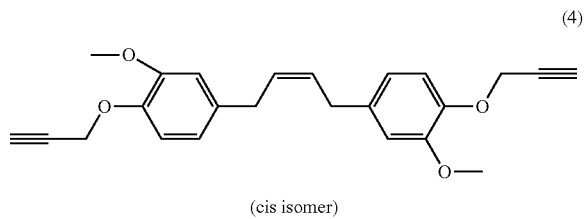

(cis isomer)

or a mixture of these two isomers.

Propargylated isoeugenol thus has the following general formula:

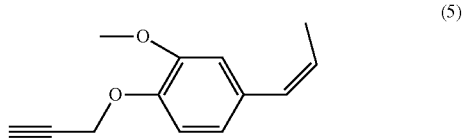

Propargylated coupled isoeugenol thus has the following general formula:

(6)

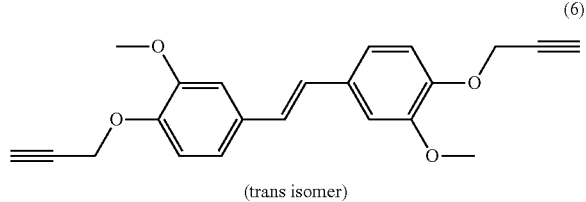 [SMILES: C#CCOc1ccc(/C=C/c2ccc(OCC#C)c(OC)c2)cc1OC]

(trans isomer)

or the following general formula (7)

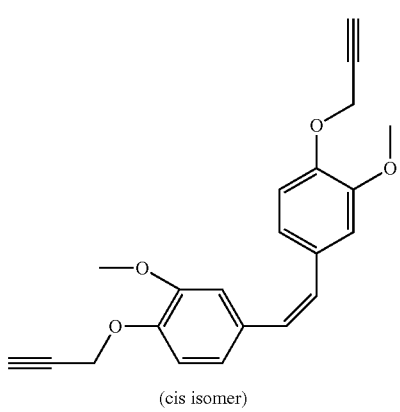

(cis isomer)

or a mixture of these two isomers.

The thermolysis may take place in the presence of a solvent. This solvent must be able to dissolve the aromatic propargyl ether of general formula (I) which is thus in dissolved form during the thermolysis. This solvent must also be inert at the temperatures involved. It serves as a dispersing gas. This solvent may beneficially be an organic solvent such as toluene. In a beneficial embodiment, the aromatic propargyl ether of general formula (I) is dissolved beforehand in a solvent, beneficially toluene, before the flash thermolysis step. Beneficially, the process according to the present invention comprises an additional step of removing the solvent, in particular by evaporation.

The thermolysis may also take place without the use of a solvent. In this case, the aromatic propargyl ether of general formula (I) may be introduced into the thermolysis device by gravity or by evaporation/sublimation, beneficially by evaporation/sublimation. In one beneficial embodiment, the aromatic propargyl ether of general formula (I) is first evaporated/sublimed before the flash thermolysis step, for example at a temperature of 130° C. and a pressure of 5.5 Pa when the compound of general formula (I) is propargylated resorcinol. The temperature of the flash thermolysis is between 300 and 600° C., beneficially between 350 and 550° C., more beneficially between 380 and 500° C., in particular between 400 and 450° C.

The pressure of the flash thermolysis is between 3 and 10,000 Pa, beneficially between 4 and 10,000 Pa, more beneficially between 5 and 7000 Pa. In the case where the flash thermolysis is performed in the presence of a solvent, the pressure is beneficially between 4000 and 10,000 Pa, more beneficially between 5000 and 7000 Pa; even more beneficially, it is 6000 Pa. In the case where the flash thermolysis is performed without solvent and where the product is first evaporated/sublimed, the pressure is beneficially between 4 and 10 Pa, more beneficially between 4.5 and 7 Pa; even more beneficially, it is 5.5 Pa.

The principle of the flash thermolysis process according to the invention is to spatially separate the molecules to promote the intramolecular reactions, and to eliminate the side intermolecular reactions; the intermolecular reactions notably include the polymerization reactions between chromene units. This spatial separation takes place by placing the reaction column under vacuum, the reagent being in the gas phase during its intramolecular rearrangement. The reaction times are very short, generally less than a second.

The process according to the invention thus consists in introducing a precursor in the gas phase into a column preheated to a very high temperature and then in rapidly condensing the product leaving the column. The reaction column is generally filled with an inert solid, such as quartz or glass beads, so as to ensure the heat exchange between the reagent and the furnace. Beneficially, the column is a glass column of defined length and width, for example with a length of between 55 and 75 cm, beneficially between 60 and 65 cm, in particular 64 cm, and a diameter of between 20 and 40 mm, in particular 30 mm, filled, for example, with glass beads with a diameter of between 2 and 10 mm, beneficially 4 mm (±0.3 mm).

The device may also comprise a vertical tube furnace, and a receiving vessel of sufficient volume, cooled with liquid nitrogen. It may furthermore comprise a dropping funnel via which the reagent is introduced when the thermolysis is performed in the presence of a solvent, and a connection to a membrane pump, for achieving the necessary vacuum. It may moreover comprise, instead of the membrane pump, a vane pump to obtain a higher vacuum, and a means for heating the reagent (such as a heating strip, a furnace or a hot-air gun) in the case where the reagent is evaporated/sublimed before the thermolysis, and also a horizontal tube for introducing the reagent.

The apparatus used for flash thermolysis is well known to those skilled in the art and is in particular described in the prior art.

The inventors realised that it was not necessary to have quantitative conversion of the propargyl ether functions into chromene in order to obtain an enthalpy of polymerization of less than 500 J/g. Specifically, the energy released during the polymerization for a given substrate is dependent on its molar mass and on its functionality. By using the energy released per propargyl function and per chromene function, combined with the molar mass of each substrate, it is possible theoretically to determine the maximum percentage of residual propargyl functions in order to be below 500 J/g. These values were compared with the experimental values obtained and are similar. Thus, Table 1 below indicates the theoretical percentage of residual propargyl functions in order to be below the 500 J/g of enthalpy of reaction during the polymerization. The theoretical percentage of residual propargyl functions is calculated in the following manner: (number of moles of propargyl functions at the end of the reaction)/(number of moles of propargyl functions before the start of the reaction)×100.

TABLE 1

| Substrate | M (g/mol) | Propargyl group functionality | Theoretical molar percentage of residual propargyl functions to achieve an enthalpy of 500 J/g |
|---|---|---|---|
| Propargylated resorcinol | 186.21 | 2 | 11 |

TABLE 1-continued

| Substrate | M (g/mol) | Propargyl group functionality | Theoretical molar percentage of residual propargyl functions to achieve an enthalpy of 500 J/g |
|---|---|---|---|
| Propargylated coupled eugenol | 376.44 | 2 | 39 |
| Propargylated coupled isoeugenol | 348.39 | 2 | 35 |

Thus, beneficially, the conversion of the aromatic propargyl ethers into chromene by the process according to the present invention is not total and the chromene obtained comprises residual propargyl functions. Beneficially, the molar percentage of residual propargyl functions in the chromene is less than 11% when the aromatic propargyl ether of general formula (I) is propargylated resorcinol, the molar percentage of residual propargyl functions in the chromene is less than 39% when the aromatic propargyl ether of general formula (I) is propargylated coupled eugenol and the molar percentage of residual propargyl functions in the chromene is less than 35% when the aromatic propargyl ether of general formula (I) is propargylated coupled isoeugenol.

In the case where the aromatic propargyl ether of general formula (I) is propargylated resorcinol, the chromene obtained by means of the process according to the invention may have the formula C and/or D below; beneficially, it is a mixture of formulae C and D.

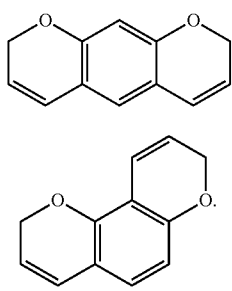

(C)

(D)

In particular, the process according to the invention promotes the formation of compound D relative to C. The molar proportions may thus be beneficially between 75% and 96% as a function of the operating conditions.

In the case where the aromatic propargyl ether of general formula (I) is propargylated resorcinol, the chromene obtained by means of the process according to the invention may also have the formula A and/or B below

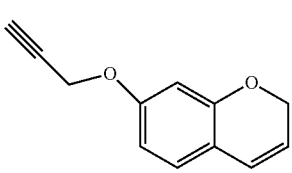

(A)

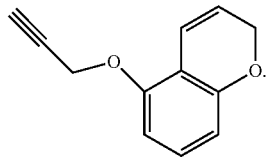

(B)

However, these molecules are generally rapidly converted into compounds of formulae C and D.

Beneficially, the molar yield of the reaction for the conversion of the aromatic propargyl ether into chromene is between 60% and 99%, in particular between 65% and 99%.

The present invention also relates to a process for preparing a material made of thermoset resin, comprising the following successive steps:
a) implementation of the process according to the present invention, beneficially as described above;
b) polymerization of the reaction product obtained in step a) so as to obtain the material made of thermoset resin;
c) recovery of the material made of thermoset resin obtained in step b).

In accordance with the invention, the polymerization of the resin may be performed via any means that is capable of inducing the polymerization/crosslinking of the chromene, and notably by applying a heat treatment or a light treatment (visible, UV or IR light).

In particular, step b) is performed by heat treatment, beneficially at a temperature of between 80° C. and 180° C., more beneficially by means of several stationary heating stages (in particular 5), without addition of other components, for instance 2 hours at 80° C., 2 hours at 100° C., 2 hours at 110° C., 2 hours at 120° C., 2 hours at 130° C. and 2 hours at 150° C. More particularly, the process according to the invention may comprise between steps b) and c) an annealing step b1) at a temperature above 200° C. but below the degradation temperature of the resin, for example at 220° C. This step enables the thermomechanical properties of the resin to be improved.

Beneficially, the enthalpy of polymerization of step b) is less than 500 J/g. Beneficially, the coke content of the thermoset resin obtained in step b) is greater than 50%.

In a beneficial embodiment, the material made of thermoset resin is a material forming the matrix of a composite material of the type comprising a matrix in which a reinforcement is present.

The reinforcement present in the composite material may be of various types. Thus, it may notably be a reinforcement consisting of fibres such as glass fibres, quartz fibres, carbon fibres, graphite fibres, silica fibres, metal fibres such as steel fibres or aluminium fibres, boron fibres, ceramic fibres such as silicon carbide fibres or boron carbide fibres, synthetic organic fibres such as aramid fibres, polyethylene fibres, polyester fibres or poly(p-phenylene benzobisoxazole) fibres, more commonly known by the abbreviation PBO, natural organic fibres such as hemp fibres, flax fibres or silk fibres, or alternatively mixtures of such fibres, in which case this reinforcement may be, depending on the nature of the fibres of which it is constituted, in the form of chopped yarns, of ground fibres, of continuous filament mats, of chopped filament mats, of stratifils (or "rovings"), of fabrics, of knitted fabrics, of felts, etc., or else in the form of complexes made by combination of various types of flat materials.

It may also be a reinforcement consisting of particles such as cork particles or refractory fillers such as tungsten, magnesium oxide, calcium oxide, alumina, silica, zirconium dioxide, titanium dioxide, beryllium oxide, etc.

Moreover, the manufacture of the composite material, and thus the addition of reinforcement to the resin, may be performed by any technique known to a person skilled in the art of composite materials, for instance by impregnation, by simultaneous injection-moulding, by autoclave drape moulding, by vacuum moulding, by moulding by low-pressure injection of resin (or "resin transfer moulding", RTM), by low-pressure "wet-route" cold-press moulding, by compound injection moulding (or "bulk moulding compound", BMC), by moulding by compression of preimpregnated mats (or "sheet moulding compound", SMC), by filament winding, by centrifugation or by pultrusion, impregnation being preferred in the case where the reinforcement consists of fibres.

Beneficially, the composite material is an ablative composite material and, more specifically, a thermal-protection ablative composite material, notably for the aerospace industry.

The present invention will be understood more clearly on reading the description of the examples that follow, which are given as non-limiting guides.

The device used for the examples comprises a glass reaction column 64 cm long and with a diameter of 3 cm, filled with spherical glass beads 4 mm (±0.3 mm) in diameter, so as to ensure the heat exchange between the reagent and the furnace, a vertical electrical tube furnace, and a receiving vessel of sufficient volume, cooled with liquid nitrogen. The device also comprises a dropping funnel by which the reagent is introduced when the thermolysis is performed in the presence of a solvent, and a connection to a membrane pump, for achieving the necessary vacuum when this vacuum is between 1000 and 6000 Pa. The device comprises a horizontal introduction tube surrounded with heating strips when the reagent is evaporated/sublimed before the thermolysis. A vane pump is used instead of the membrane pump to obtain a vacuum of 5.5 Pa.

EXAMPLE 1

Conversion of Propargylated Resorcinol and Preparation of the Resin According to the Invention Synthesis of Propargylated Resorcinol
10 g (0.091 mol) of resorcinol (Alfa Aesar) are dissolved in 50 mL of dimethyl sulfoxide (DMSO), 50 g (0.363 mol) of potassium carbonate ($K_2CO_3$) are ground and then added with magnetic stirring, and the medium is heated to 70° C. (ext). 14.45 mL (2.2 eq.) of propargyl chloride (ABCR) are added dropwise. The reaction is monitored by TLC with a ⅔ (volume) petroleum ether/diethyl ether eluent. After filtration and dilution in 100 mL of ethyl acetate, the medium is extracted with 3×100 mL of brine. The organic phase is dried over $MgSO_4$, filtered and concentrated under reduced pressure. The compound is purified by vacuum distillation (T° C.=120° C., 4.5 Pa). The yield is 77.4%.

Conversion of Propargylated Resorcinol
0.5 g (0.0027 mol) of propargylated resorcinol obtained previously is dissolved in 20 mL of toluene and placed in the dropping funnel at the top of the column. The reagent is introduced into the column at an average rate of 0.5 mL/minute into a column preheated to between 410° C. and 430° C. under a vacuum of 6000 Pa. After elution of all of the reagent and cooling of the column, the vacuum is broken and the product is recovered. The toluene is evaporated off under reduced pressure on a rotary evaporator and the product is then dried using a vane pump. The crude yield obtained is 85%. The proportion of residual propargyl functions is estimated by $^1H$ NMR as less than 1%. The crude product is composed of 13 mol % of C and 79.2 mol of D. The molar proportion of compound of 2-indanone type is 7.8%. The molar proportion of residual propargyl functions of less than 11% complies with the set specifications.

Polymerization of the Chromene Obtained from Proparaylated Resorcinol
The polymerization of the propargyl-chromene mixtures is performed by gradual raising of the temperature. In the case of a propargyl resorcinol-chromene mixture with a proportion of residual propargyl ether functions of less than 11% as obtained previously, the heat treatment applied is as follows: 2 hours at 80° C., 2 hours at 100° C., 2 hours at 110° C., 2 hours at 120° C., 2 hours at 130° C. and 2 hours at 150° C.

Annealing at 220° C. may be performed to increase the thermomechanical properties.

The coke content before or after annealing is 64.3% and the enthalpy of reaction is 280 J/g.

Example 2

Conversion of Propargylated Resorcinol

Conversion of Propargylated Resorcinol
10 g (0.0537 mol) of propargylated resorcinol obtained as in Example 1 are dissolved in 350 mL of toluene and placed in the dropping funnel at the top of the column. The reagent is introduced at an average rate of 1.5 mL/minute into a column preheated to between 420° C. and 430° C. under a vacuum of 6000 Pa. After elution of all of the reagent and cooling of the column, the vacuum is broken and the product is recovered. The toluene is evaporated off under reduced pressure on a rotary evaporator and the product is then dried using a vane pump. The crude yield is 83.4%. The proportion of residual propargyl functions is estimated by $^1H$ NMR at 2.2%. The crude product is composed of 4.4 mol % of C and 71.3 mol % of D. The molar proportion of compound of 2-indanone type is 23.1%. The molar proportion of residual propargyl functions of less than 11% complies with the set specifications.

Example 3

Conversion of Propargylated Eugenol and Preparation of the Resin According to the Invention Synthesis of Propargylated Eugenol
Eugenol (Sigma-Aldrich) (200 g), $K_2CO_3$ (211 g) and dimethylformamide (DMF) (2000 mL) are placed in a 6 L round-bottomed flask and heated to 75° C. with mechanical stirring. Propargyl chloride (ABCR) at 70% in toluene (158.5 mL) is added dropwise via a dropping funnel, and the reaction medium is heated and stirred at 75° C. overnight. The reaction is monitored by TLC, eluting with ⅔ (volume) petroleum ether/diethyl ether. After the reaction, the reaction medium is filtered and then diluted and rinsed with ethyl acetate. The organic phase is rinsed with water until the aqueous phase has decolourized (four times). The organic phase is dried over $MgSO_4$ and concentrated under vacuum. The yield of crude product is 93%. The compound is purified by vacuum distillation (p=4.5 Pa and T° C.=60° C.). The yield of the distilled compound is 90%.

Conversion of Propargylated Eugenol 0.5 g (0.0054 mol) of propargylated eugenol obtained previously is dissolved in 20 mL of toluene and placed in the dropping funnel at the top of the column. The reagent is introduced into the column at an average rate of 0.5 mL/minute into a column preheated to between 410° C. and 420° C. under a vacuum of 6000 Pa. After elution of all of the reagent and cooling of the column, the vacuum is broken and the product is recovered. The toluene is evaporated off under reduced pressure on a rotary evaporator and the product is then dried using a vane pump. The crude yield is 65%. The proportion of residual propargyl functions is estimated by $^1$H NMR at 0%. The molar proportion of chromene compound is estimated by $^1$H NMR at 54%. The parent phenolic compound of the propargyl ether compound, eugenol, is formed to a proportion of 46 mol %.

Polymerization of the Chromene Obtained from Proparaylated Eugenol

The process performed is identical to that described in Example 1 for propargylated resorcinol.

Example 4

Conversion of Propargylated Isoeugenol and Preparation of the Resin According to the Invention Synthesis of Propargylated Isoeugenol 20 g (0.130 mol) of isoeugenol (Sigma-Aldrich) are dissolved in 100 mL (5 eq.) of DMF. 33.67 g (2 eq.) of finely ground potassium carbonate ($K_2CO_3$) are added with magnetic stirring. 20.35 mL (1.5 eq.) of propargyl bromide (Alfa Aesar) (80 mol % in toluene) are added via the dropping funnel. Magnetic stirring is continued for 12 hours. Completion of the reaction is monitored by TLC, eluting with 70/30 (volume) petroleum ether/ethyl acetate. After filtering off the $K_2CO_3$ and washing with ethyl acetate, 100 mL of ethyl acetate are added to the medium for the extraction. The organic phase is washed three times with distilled water (3×100 mL) and once with brine (1×100 mL). The organic phase is dried over $MgSO_4$, filtered and concentrated under reduced pressure. The yield is 91%.

The compound is purified by vacuum distillation in a Kugelrohr glass oven (p=15 Pa and heating T° C.=140° C.). The compound is recovered in the form of white crystals. The overall yield after purification is 73%.

Conversion of the Proparaylated Isoeugenol 0.5 g (0.0054 mol) of propargylated isoeugenol obtained previously is dissolved in 20 mL of toluene and placed in the dropping funnel at the top of the column. The reagent is introduced into the column at an average rate of 0.5 mL/minute into a column preheated to between 410° C. and 420° C. under a vacuum of 6000 Pa. After elution of all of the reagent and cooling of the column, the vacuum is broken and the product is recovered. The toluene is evaporated off under reduced pressure on a rotary evaporator and the product is then dried using a vane pump. The crude yield is 65%. The molar proportion of residual propargyl functions is estimated by $^1$H NMR at 0%. The molar proportion of chromene compound is estimated by $^1$H NMR at 43%. The parent phenolic compound of the propargyl ether compound, isoeugenol, is formed to a proportion of 57 mol % of the mixture during the reaction.

Polymerization of the Chromene Obtained from Proparaylated Isoeugenol

The process performed is identical to that described in Example 1.

Example 5

Conversion of Propargylated Resorcinol in the Absence of Solvent and with Sublimation/Evaporation of the Reagent and Preparation of the Resin According to the Invention Conversion of Propargylated Resorcinol 4 g (0.021 mol) of propargylated resorcinol obtained as in Example 1 are dispersed in 50 g of glass beads 4 mm in diameter and placed in a horizontal tube at the top of the column. The column is preheated to between 410 and 420° C. The thermolysis device is placed under a vacuum of 5.5 Pa. The horizontal tube containing the reagent is gradually heated to a temperature of 130° C., allowing the gradual evaporation/sublimation of the reagent and its passage into the column. The product is recovered at the outlet in a trap cooled with liquid nitrogen. After elution of all of the reagent and cooling of the column, the vacuum is broken and the product is recovered. The crude yield is 90%. The proportion of residual propargyl functions is estimated by $^1$H NMR at 0%. The crude product is composed of 14 mol % of C and 79 mol % of D. The molar proportion of compound of 2-indanone type is 7%. The molar proportion of residual propargyl functions of less than 11% complies with the set specifications.

Polymerization of the Chromene Obtained from Propargylated Resorcinol

The process performed is identical to that described in Example 1.

Example 6

Conversion of Propargylated Resorcinol in the Absence of Solvent and Preparation of the Resin According to the Invention 8 g (0.043 mol) of propargylated resorcinol obtained as in Example 1 are introduced neat into the dropping funnel at the top of the column. The dropping funnel is heated to 40° C. to change the state of the reagent from solid to liquid. The reagent is introduced into the column at an average rate of 0.5 mL/minute into a column preheated to between 410° C. and 420° C. under a vacuum of 6000 Pa. After elution of all of the reagent and cooling of the column, the vacuum is broken and the product is recovered. The crude yield is 7%. The proportion of residual propargyl functions is estimated by $^1$H NMR at 0%. The crude product is composed of 3.3 mol % of C and 79.7 mol % of D. The molar proportion of compound of 2-indanone type is 17%.

Polymerization of the Chromene Obtained from Proparaylated Resorcinol The process performed is identical to that described in Example 1.

COMPARATIVE EXAMPLE 1

Attempted Conversion of Propargylated Resorcinol 1 g (0.0054 mol) of propargylated resorcinol obtained as in Example 1 is dissolved in 40 mL of toluene and placed in the dropping funnel at the top of the column. The reagent is introduced into the column at an average rate of 0.5 mL/minute into a column preheated to between 250° C. and 270° C. under a vacuum of 1000 Pa. After elution of all of the reagent and cooling of the column, the vacuum is broken and the product is recovered. The toluene is evaporated off under reduced pressure on a rotary evaporator and the product is then dried using a vane pump. The crude yield is 92%. The proportion of residual propargyl functions is estimated by $^1$H NMR at 100%. The proportion of residual propargyl functions of greater than 11% is not in compliance with the set specifications.

The temperature is thus an important parameter for obtaining the conversion of propargylated resorcinol into chromene according to the set specifications.

The invention claimed is:

1. A process for manufacturing chromenes which are intended for the preparation of thermosetting resins, comprising the step of transforming an aromatic propargyl ether of general formula (I) below

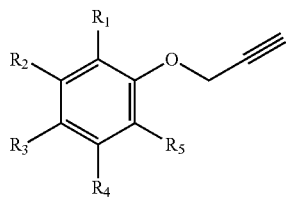

(I)

in which:

$R_1$ and $R_5$ represent, independently of each other, a hydrogen atom, a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group, on condition that at least one from among $R_1$ and $R_5$ represents a hydrogen atom;

$R_2$ and $R_4$ represent, independently of each other, a hydrogen atom, a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group;

and $R_3$ represents a hydrogen atom, a O—($C_1$-$C_6$)alkyl or a $C_2$-$C_6$ alkene group, the alkene group being optionally substituted with a group of general formula (II) below

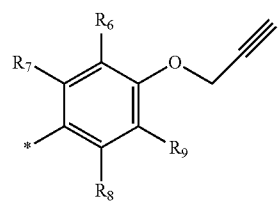

(II)

in which:

$R_6$ and $R_9$ represent, independently of each other, a hydrogen atom, a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group, on condition that at least one from among $R_6$ and $R_9$ represents a hydrogen atom;

and $R_7$ and $R_8$ represent, independently of each other, a hydrogen atom, a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group;

on condition that at least one from among $R_1$, $R_2$, $R_3$, $R_4$ and $R_5$ does not represent a hydrogen atom or a O—($C_1$-$C_6$)alkyl group;

and the cis/trans isomers thereof and the optical isomers thereof and the racemic mixtures thereof into a chromene by flash vacuum thermolysis, at a temperature of between 300 and 600° C., at a pressure of between 4 and 10,000 Pa, wherein the aromatic propargyl ether of general formula (I) is chosen from the group consisting of propargylated resorcinol, propargylated eugenol, propargylated coupled eugenol, propargylated coupled isoeugenol, propargylated isoeugenol and mixtures thereof and the cis/trans isomers thereof and the optical isomers thereof and the racemic mixtures thereof.

2. The process according to claim 1, wherein the molar percentage of residual propargyl functions in the chromene is less than 11% when the aromatic propargyl ether of general formula (I) is propargylated resorcinol, the molar percentage of residual propargyl functions in the chromene is less than 39% when the aromatic propargyl ether of general formula (I) is propargylated coupled eugenol and the molar percentage of residual propargyl functions in the chromene is less than 35% when the aromatic propargyl ether of general formula (I) is propargylated coupled isoeugenol.

3. The process according to claim 1, wherein the aromatic propargyl ether of general formula (I) is dissolved beforehand in a solvent before the flash thermolysis step.

4. The process according to claim 1, wherein the aromatic propargyl ether of general formula (I) is first evaporated/sublimed, before the flash thermolysis step.

5. The process according to claim 1, which is a continuous process.

6. The process according to claim 1, wherein the aromatic propargyl ether of general formula (I) is propargylated resorcinol and wherein the chromene obtained has the formula C and/or D below

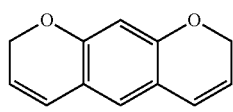

(C)

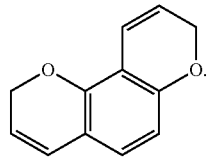

(D)

7. A process for preparing a material made of thermoset resin, comprising the following successive steps:
 a) implementation of the process according to claim 1;
 b) polymerization of the reaction product obtained in step a) so as to obtain the material made of thermoset resin;
 c) recovery of the material made of thermoset resin obtained in step b).

8. The process according to claim 7, wherein the enthalpy of polymerization of step b) is less than 500 J/g.

9. The process according to claim 7, wherein the coke content of the thermoset resin obtained in step c) is greater than 50% by mass.

10. The process according to claim 1, wherein the temperature is of between 400 and 450° C.

11. The process according to claim 1, wherein the pressure is of between 5 and 7000 Pa.

12. The process according to claim 1, wherein the aromatic propargyl ether of general formula (I) is propargylated resorcinol.

13. The process according to claim 3, wherein the solvent is toluene.

14. The process according to claim 6, wherein the chromene obtained is a mixture of the formulae C and D.

* * * * *